United States Patent [19]
Or et al.

[11] Patent Number: 5,780,605
[45] Date of Patent: Jul. 14, 1998

[54] 6,9-BRIDGED ERYTHROMYCIN DERIVATIVES

[75] Inventors: Yat Sun Or, Libertyville; Richard F. Clark, Mundelein, both of Ill.; Daniel T. Chu, Santa Clara, Calif.; Jacob J. Plattner, Libertyville, Ill.

[73] Assignee: Abbott Laboratories, Abbott Park, Ill.

[21] Appl. No.: 925,582

[22] Filed: Sep. 8, 1997

[51] Int. Cl.$^6$ .......................... C07H 17/08; A61K 31/70
[52] U.S. Cl. .................. 536/7.2; 514/29; 536/7.4; 536/18.6
[58] Field of Search .............. 514/29; 536/7.2, 536/7.4, 18.6

[56] References Cited

U.S. PATENT DOCUMENTS

| | | | |
|---|---|---|---|
| 5,434,140 | 7/1995 | Kobrehel et al. | 514/30 |
| 5,578,579 | 11/1996 | Lartey et al. | 514/29 |
| 5,631,355 | 5/1997 | Asaka et al. | 536/7.4 |
| 5,635,485 | 6/1997 | Agouridas et al. | 514/29 |
| 5,658,888 | 8/1997 | Koga et al. | 514/29 |
| 5,712,253 | 1/1998 | Lartey et al. | 514/28 |

FOREIGN PATENT DOCUMENTS

| | | |
|---|---|---|
| 0215335 A | 3/1987 | European Pat. Off. |
| 0272110 A | 6/1988 | European Pat. Off. |

OTHER PUBLICATIONS

Journal of Antibiotics, vol. 37, No. 2, (1984), pp. 187–189, S. Morimoto et al., "Chemical Modification of Erythromycins. I. Synthesis and Antibacterial Activity of 6-O-Methylerythromycins A".

Journal of Antibiotics, vol. 43, No. 3 (1990), pp. 286–294, S. Morimoto et al., "Chemical Modification of Erythromycins. II. Synthesis and Antibacterial Activity of O-Alkyl Derivatives of Erythromycin A".

Primary Examiner—John Kight
Assistant Examiner—Howard C. Lee
Attorney, Agent, or Firm—Mona Anand

[57] ABSTRACT

Novel multicyclic erythromycin compounds and pharmaceutically acceptable salts and esters thereof having antibacterial activity having a formula

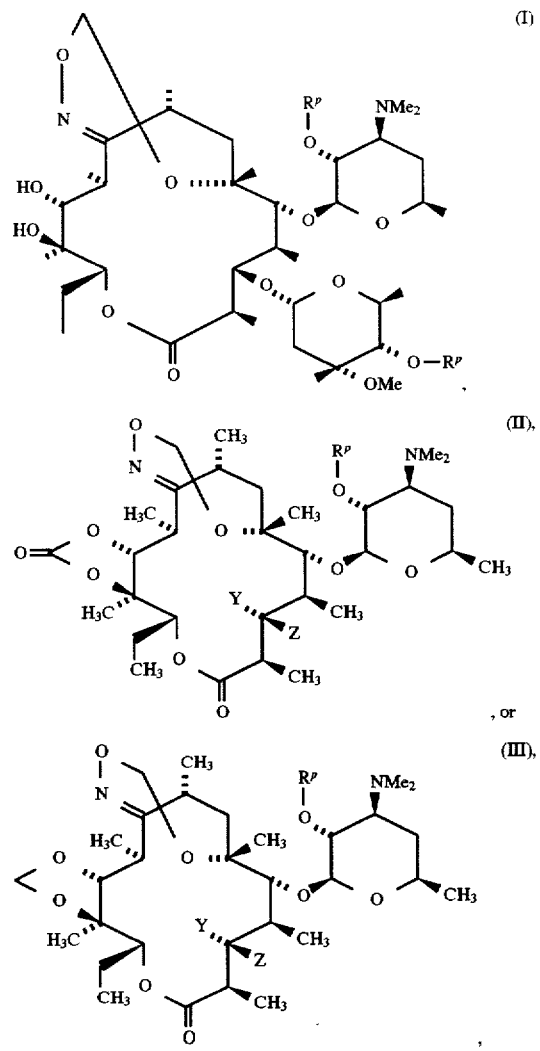

compositions comprising a therapeutically effective amount of a compound of the invention in combination with a pharmaceutically acceptable carrier, as well as a method for treating bacterial infections by administering to a mammal a pharmaceutical composition containing a therapeutically-effective amount of a compound of the invention.

9 Claims, No Drawings

6,9-BRIDGED ERYTHROMYCIN DERIVATIVES

TECHNICAL FIELD

The present invention relates to semisynthetic macrolides having antibacterial activity and useful in the treatment and prevention of bacterial infections. More particularly, the invention relates to 6,9-bridged erythromycin derivatives, compositions containing such compounds and methods for using the same, as well as processes for making such compounds.

BACKGROUND OF THE INVENTION

Erythromycins A through D, represented by formula (E),

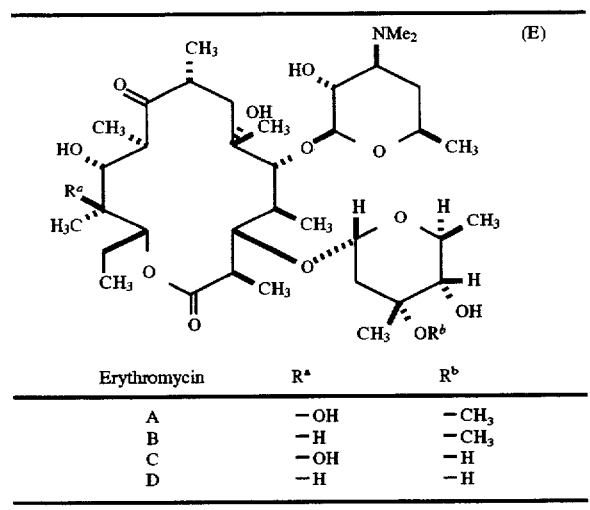

| Erythromycin | $R^a$ | $R^b$ |
|---|---|---|
| A | —OH | —$CH_3$ |
| B | —H | —$CH_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Morimoto et al. described the preparation of 6-O-methyl erythromycin A in *J. Antibiotics* 37:187 (1984). Morimoto et al. further disclosed a series of O-alkyl erythromycin A derivatives in *J. Antibiotics* 43: 286 (1990). In their experience, "O-alkylation, other than methylation, took place at the C-11 hydroxyl group exclusively." However, in European Patent Application 272,110, published Jun. 22, 1988, Morimoto et al. disclose 6-O—$C_1$-$C_3$-alkyl erythromycin A compounds.

In European Patent Application 215,355, published Mar. 28, 1987, Omura and Itoh disclose 6O-loweralkyl erythromycins as stimulants of gastrointestinal contractile motion.

SUMMARY OF THE INVENTION

The present invention provides a novel class of 6,9-bridged erythromycin compounds which possess antibacterial activity.

In one aspect of the present invention are compounds, or pharmaceutically acceptable salts and esters thereof, having a formula selected from the group consisting of

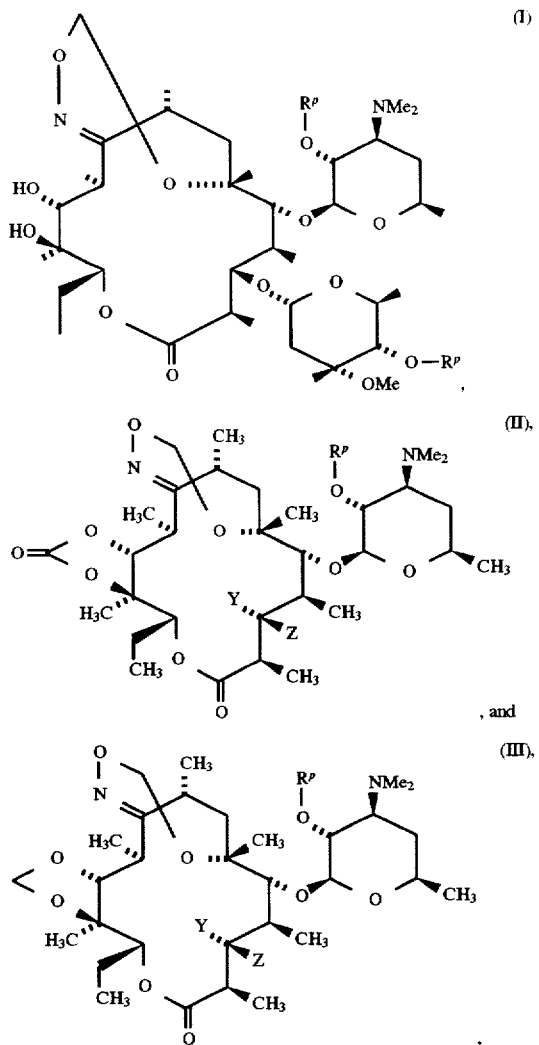

as well as the pharmaceutically acceptable salts, esters and prodrugs thereof, wherein $R^p$ is hydrogen or a hydroxy protecting group;

one of Y and Z is H and the other is selected from the group consisting of hydrogen, hydroxy, protected hydroxy and —O-cladinose, or Y and Z are taken together with the atom to which they are attached to form an oxo group.

In another aspect of the present invention are disclosed pharmaceutical compositions for treating bacterial infections comprising a therapeutically effective amount of a compound of the invention in combination with a pharmaceutically acceptable carrier. Suitable carriers and methods of formulation are also disclosed.

Still another aspect of this invention is a method for treating bacterial infections comprising administering to a mammal in need of such treatment a pharmaceutical composition containing a therapeutically-effective amount of a compound of the invention.

In a further aspect of the invention are provided processes for the preparation of 6,9-bridged macrolide compounds of Formula (I)–(II) above.

DETAILED DESCRIPTION OF THE INVENTION

In a first embodiment of the invention is a compound having the formula (I) as described above.

In a second embodiment of the invention is a compound having the formula (II) as described above.

In a third embodiment of the invention is a compound having the formula (III) as described above.

Representative compounds of the invention are those selected from the group consisting of:

Compound of formula (I) Rp is H;

Compound of formula (II) $R^p$ is H, Y is H, Z is cladinose;

Compound of formula (II), $R^p$ is H, Y and Z taken together with the atom to which they are attached form an oxo group.

Compound of formula (III), $R^p$ is H, Y is H and Z is hydroxy;

Compound of formula (III), $R^p$ is H, Y and Z are H; and

Compound of formula (III), $R^p$ is H, Y and Z taken together with the atom to which they are attached form an oxo group.

One aspect of the invention is a process for preparing a compound having the formula (I)

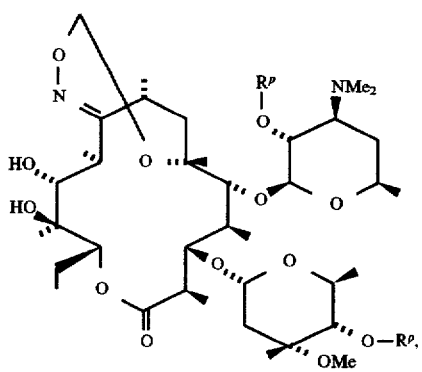

(I)

wherein $R^p$ is hydrogen or a hydroxy protecting group; the method comprising:

(a) reacting a compound having the formula

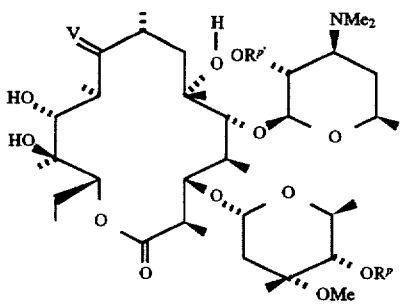

wherein $R^{p'}$ is a hydroxy protecting group; and

V is $=N-O-R^1$ or $=N-O-C(R^2)(R^3)-O-R^1$, wherein $R^1$ is selected from the group consisting of:
(c-1) $C_1-C_6$-alkyl,
(c-2) $C_1-C_6$-alkyl substituted with one or more groups selected from the group consisting of
(c-2-a) aryl,
(c-2-b) substituted aryl,
(c-d-c) heteroaryl,
(c-2-d) substituted heteroaryl,
(c-2-e) heterocycloalkyl,
(c-2-f) $C_1-C_6$-alkoxy, $R^2$ and $R^3$ are each independently selected from the group consisting of
(a) hydrogen,
(b) unsubstituted $C_1-C_{12}$-alkyl,
(c) $C_1-C_{12}$-alkyl substituted with aryl, and
(d) $C_1-C_{12}$-alkyl substituted with substituted aryl, or $R^2$ and $R^3$ taken together with the carbon to which they are attached form a $C_3-C_{12}$-cycloalkyl ring;

with bromofluoromethane in the presence of base to give a compound having the formula

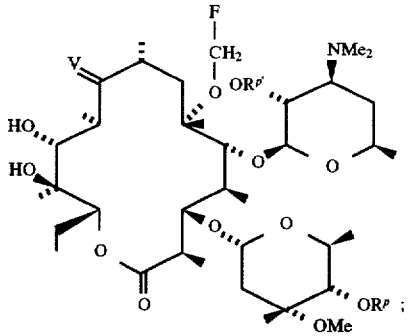

(b) treating the compound from Step (a) hydrolytically with acid to give a compound having the formula

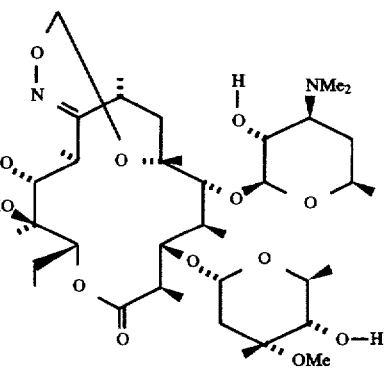

(c) optionally treating the compound from Step (b) with a hydroxy protecting reagent to give the desired compound wherein $R^p$ is a hydroxy protecting group.

Another aspect of the invention is a process for preparing a compound having the formula (II)

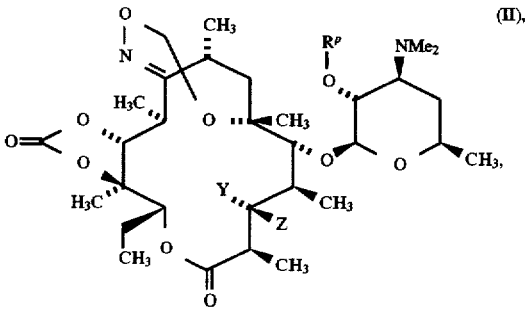

(II), wherein $R^p$ is hydrogen or a hydroxy protecting group;

one of Y and Z is H and the other is selected from the group consisting of hydrogen, hydroxy, protected hydroxy and —O-cladinose, or Y and Z are taken together with the atom to which they are attached to form an oxo group.

the method comprising:

(a) reacting a compound having the formula

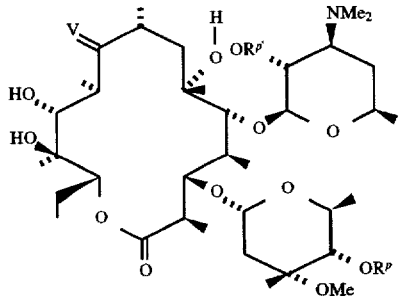

wherein $R^{p'}$ is a hydroxy protecting group; and

V is $=N-O-R^1$ or $=N-O-C(R^2)(R^3)-O-R^1$, wherein $R^1$ is selected from the group consisting of:
(c-1) $C_1-C_6$-alkyl,
(c-2) $C_1-C_6$-alkyl substituted with one or more groups selected from the group consisting of
 (c-2-a) aryl,
 (c-2-b) substituted aryl,
 (c-d-c) heteroaryl,
 (c-2-d) substituted heteroaryl,
 (c-2-e) heterocycloalkyl,
 (c-2-f) $C_1-C_6$-alkoxy, $R^2$ and $R^3$ are each independently selected from the group consisting of
 (a) hydrogen,
 (b) unsubstituted $C_1-C_{12}$-alkyl,
 (c) $C_1-C_{12}$-alkyl substituted with aryl, and
 (d) $C_1-C_{12}$-alkyl substituted with substituted aryl, or $R^2$ and $R^3$ taken together with the carbon to which they are attached form a $C_3-C_{12}$-cycloalkyl ring;

with bromofluoromethane in the presence of base to give a compound having the formula

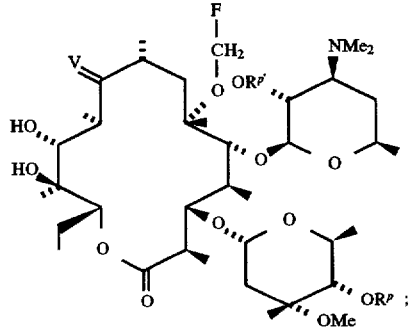

(b) treating the compound from Step (a) hydrolytically with acid to give a compound having the formula

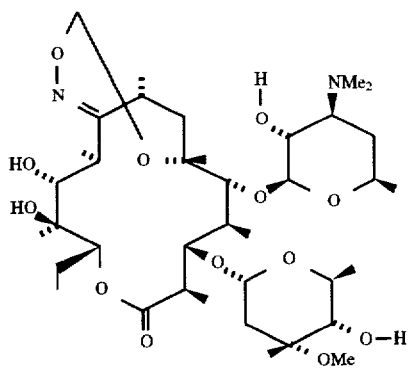

(c) treating the compound from Step (b) with a hydroxy protecting reagent to give the desired compound wherein $R^{p'}$ is a hydroxy protecting group (d) treating a compound from Step (c) with a reagent selected from the group consisting of
 (i) carbonyldiimidazole and sodium hexamethyldisilazine, and
 (ii) an alkali metal hydride and a carbonylating reagent under anhydrous conditions, to give a compound of formula (II) wherein Y is H, Z is cladinose and $R^p$ is a hydroxy protecting group, (e) optionally hydrolytically treating with acid a compound of formula (II) wherein Y is H, Z is cladinose and $R^{p'}$ is a hydroxy protecting group (the compound from Step (d)) to give a compound of formula (II) wherein Y is H, Z is hydroxy and $R^p$ is a hydroxy protecting group.

(f) optionally treating a compound of formula (II) wherein Y is H, Z is hydroxy and $R^{p'}$ is a hydroxy protecting group (the compound from Step (e)) with a hydroxy protecting reagent to give a compound of formula (II) Y is H, Z is protected hydroxy, and $R^{p'}$ is a hydroxy protecting group; p1 (g) optionally oxidizing a compound of formula (II) wherein Y is H, Z is hydroxy and $R^{p'}$ is a hydroxy protecting group (the compound from Step (e)) to give a compound of formula (II) wherein Y and Z are taken together with the atom to which they are attached to form an oxo group and $R^{p'}$ is a hydroxy protecting group;

(h) optionally treating a compound of formula (II) wherein Y is H, Z is hydroxy and $R^{p'}$ is a hydroxy protecting group (the compound from Step (e)) with an excess of NaH in an aprotic solvent followed by reaction of the intermediate anion with $CS_2$ and $CH_3I$ to form a xanthate intermediate which is then treated with $Bu_3SnH$ under an inert atmosphere in the presence of a catalytic amount of a suitable radical initiator to afford the desired compound of formula (II) wherein Y and Z are H and $R^{p'}$ is a hydroxy protecting group;

(i) optionally deprotecting to give a compound of formula (II) wherein $R^p$ is H; and isolating the desired compound.

Another aspect of the invention is a process for preparing a compound having the formula (III)

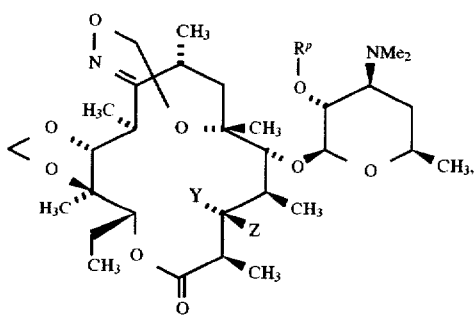

(III), wherein

R[p] is hydrogen or a hydroxy protecting group;

one of Y and Z is H and the other is selected from the group consisting of hydrogen, hydroxy, protected hydroxy and —O-cladinose, or Y and Z are taken together with the atom to which they are attached to form an oxo group.

the method comprising:

(a) reacting a compound having the formula

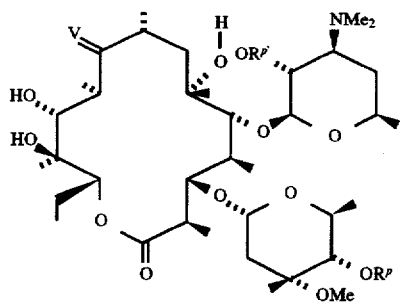

wherein R[p'] is a hydroxy protecting group; and

V is $=N-O-R^1$ or $=N-O-C(R^2)(R^3)-O-R^1$, wherein

R[1] is selected from the group consisting of:
(c-1) $C_1-C_6$-alkyl,
(c-2) $C_1-C_6$-alkyl substituted with one or more groups selected from the group consisting of
  (c-2-a) aryl,
  (c-2-b) substituted aryl,
  (c-d-c) heteroaryl,
  (c-2-d) substituted heteroaryl,
  (c-2-e) heterocycloalkyl.
  (c-2-f) $C_1-C_6$-alkoxy.

R[2] and R[3] are each independently selected from the group consisting of
(a) hydrogen,
(b) unsubstituted $C_1-C_{12}$-alkyl,
(c) $C_1-C_{12}$-alkyl substituted with aryl, and
(d) $C_1-C_{12}$-alkyl substituted with substituted aryl, or R[2] and R[3] taken together with the carbon to which they are attached form a $C_3-C_{12}$-cycloalkyl ring;

with bromofluoromethane in the presence of base to give a compound having the formula

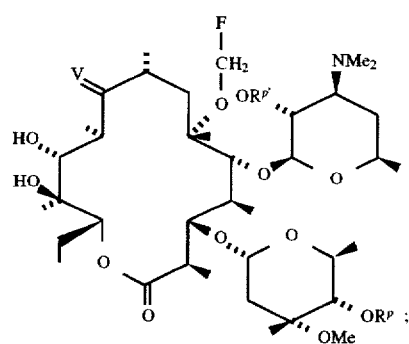

(b) treating the compound from Step (a) hydrolytically with acid to give a compound having the formula

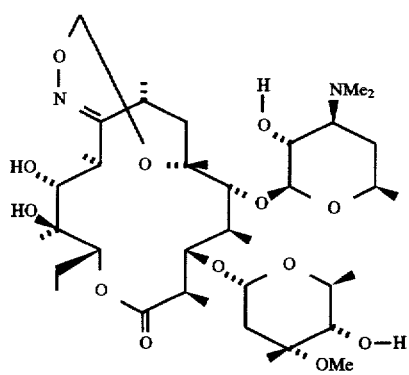

(c) treating the compound from Step (b) with a hydroxy protecting reagent to give the desired compound wherein R[p'] is a hydroxy protecting group;

(d) treating a compound from Step (c) with a reagent selected from the group consisting of
  (i) formaldehyde in the presence of an acid, and
  (ii) chloroiodomethane in the presence of base to give a compound of formula (III) wherein Y is H, Z is cladinose and R[p'] is a hydroxy protecting group;

(b) optionally hydrolytically treating with acid a compound of formula (III) wherein Y is H, Z is cladinose and R[p'] is a hydroxy protecting group (the compound from Step (d)) to give a compound of formula (III) wherein Y is H, Z is hydroxy and R[p'] is a hydroxy protecting group.

(c) optionally treating a compound of formula (II) wherein Y is H, Z is hydroxy and R[p'] is a hydroxy protecting group (the compound from Step (e)) with a hydroxy protecting reagent to give a compound of formula (III) Y is H, Z is protected hydroxy, and R[p'] is a hydroxy protecting group;

(d) optionally oxidizing a compound of formula (III) wherein Y is H, Z is hydroxy and R[p'] is hydroxy protecting group (the compound from Step (e)) to give a compound of formula (II) herein Y and Z are taken together with the atom to which they are attached to form an oxo group and R[p'] is a hydroxy protecting group;

(e) optionally treating a compound of formula (III) wherein Y is H, Z is hydroxy and R[p'] is a hydroxy protecting group (the compound from Step (e)) with an excess of NaH in an aprotic solvent followed by reaction of the intermediate anion with $CS_2$ and $CH_3I$ to form a xanthate intermediate which is then treated with Bu$_3$SnH under an inert atmosphere in the presence of a catalytic amount of a suitable radical initiator to afford the desired compound of formula (II) wherein Y and Z are H and R$^{p'}$ is a hydroxy protecting group;

(f) optionally deprotecting to give a compound of formula (III) wherein R$^p$ is H; and isolating the desired compound.

Definitions

The terms "$C_1$–$C_3$-alkyl", "$C_1$–$C_5$-alkyl", "$C_1$–$C_6$-alkyl", or "$C_1$–$C_{12}$-alkyl" as used herein refer to saturated, straight- or branched-chain hydrocarbon radicals containing between one and three, one and five, one and six, or one and twelve carbon atoms, respectively. Examples of $C_1$–$C_3$ alkyl radicals include methyl, ethyl, propyl and isopropyl, examples of $C_1$–$C_5$-alkyl radicals include, but are not limited to, methyl, ethyl, propyl, isopropyl, n-butyl, tert-butyl and neopentyl, examples of $C_1$–$C_6$-alkyl radicals include, but are not limited to methyl, ethyl, propyl, isopropyl, n-butyl, tert-butyl, neopentyl and n-hexyl, examples of $C_1$–$C_{12}$-alkyl radicals include all of the preceding examples and n-heptyl, octyl, n-decyl, n-undecyl and n-dodecyl, for example.

The term "$C_1$–$C_6$-acyl" as used herein refers to hydrogen atom or a $C_1$–$C_5$-alkyl group, as previously defined, attached to the parent molecular moiety through a carbonyl group. Examples of $C_1$–$C_6$-acyl include, but are not limited to, formyl, acetyl, propionoyl, butanoyl, pentanoyl, hexanoyl.

The term "$C_1$–$C_6$-alkoxy" as used herein refers to an $C_1$–$C_6$-alkyl group, as previously defined, attached to the parent molecular moiety through an oxygen atom. Examples of $C_1$–$C_6$-alkoxy, but are not limited to, methoxy, ethoxy, propoxy, isopropoxy, n-butoxy, tert-butoxy, neopentoxy and n-hexoxy.

The term "$C_1$–$C_3$-alkyl-amino" as used herein refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, dichloromethane, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, New York, 1986.

The term "aryl" as used herein refers to unsubstituted carbocyclic aromatic groups including, but not limited to, phenyl, 1- or 2-naphthyl and the like.

The term "$C_3$–$C_5$-cycloalkyl- and $C_3$–$C_7$-cycloalkyl" as used herein refers to carbocyclic groups of 3 to 5 or 3 to 7 carbons, respectively, for example, cyclopropyl, cyclobutyl, cyclopentyl, cyclohexyl, and cycloheptyl.

The term "$C_1$–$C_3$-alkyl-$C_3$–$C_5$-cycloalkyl", as used herein refers to a $C_3$–$C_5$-cycloalkyl radical, as defined above, attached to a $C_1$–$C_3$-alkyl radical by replacement of a hydrogen atom on the latter.

The terms "halo" and "halogen" as used herein refer to an atom selected from fluorine, chlorine, bromine and iodine.

The term "halo-$C_1$–$C_3$-alkyl" as used herein refers to a $C_1$–$C_3$-alkyl group as defined above wherein 1, 2 or 3 hydrogen atoms thereon are independently replaced by a halogen atom.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "heterocycloalkyl" as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

"Hydroxy-protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, New York, 1986.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$–$C_3$-alkyl, halo-$C_1$–$C_3$-alkyl, $C_1$–$C_6$-alkoxy, thio-$C_1$–$C_6$-alkoxy, methoxymethoxy, amino, $C_1$–$C_3$-alkyl-amino, di($C_1$–$C_3$-alkyl)amino, formyl, carboxy, alkoxycarbonyl, $C_1$–$C_3$-alkyl-CO—O—, $C_1$–$C_3$-alkyl-CO—NH—, or carboxamide; except that tetrafluorophenyl and pentafluorophenyl are also included within the definition of "substituted aryl."

The term "substituted heteroaryl" as used herein refers to a heteroaryl group as defined herein substituted by independent replacement of one, two or three of the hydrogen atoms thereon with Cl, Br, F, I, OH, $C_1$–$C_3$-alkyl, $C_1$–$C_6$-alkoxy, methoxymethoxy, amino, or $C_1$–$C_3$-alkyl-amino, or may also refer to a mono-oxo substituted heteroaryl compound, such as 4-oxo-1H-quinoline, for example.

The term "substituted heterocycloalkyl" as used herein, refers to a heterocycloalkyl group, as defined above, substituted by independent replacement of one, two or three of the hydrogen atoms thereon with Cl, Br, F, I, OH, cyano, mercapto, nitro, $C_1$–$C_3$-alkyl, halo-$C_1$–$C_3$-alkyl, $C_1$–$C_6$-alkoxy, thio-$C_1$–$C_6$-alkoxy, methoxymethoxy, amino, $C_1$–$C_3$-alkyl-amino, di($C_1$–$C_3$-alkyl)amino, carboxaldehydo, carboxy, alkoxycarbonyl, $C_1$–$C_3$-alkyl-CO—O—, $C_1$–$C_3$-alkyl-CO—NH—, or carboxamide.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Prodrugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35°–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 2 demonstrate the antibacterial activity of the compounds of the invention.

TABLE 1

Antibacterial Activity (MIC's) of Selected Compounds

| Microorganism | Ery. A standard | Example 1 | Example 2 | Example 3 |
|---|---|---|---|---|
| Staphylococcus aureus ATCC 6538P | 0.2 | 6.2 | 0.39 | 3.1 |
| Staphylococcus aureus A5177 | 3.1 | >100 | 3.1 | 3.1 |
| Staphylococcus aureus A-5278 | >100 | >100 | >100 | >100 |
| Staphylococcus aureus CMX 642A | 0.39 | 12.5 | 0.39 | 3.1 |
| Staphylococcus aureus NCTC10649M | 0.39 | 6.2 | | 3.1 |
| Staphylococcus aureus CMX 553 | 0.39 | 6.2 | 0.78 | 3.1 |
| Staphylococcus aureus 1775 | >100 | >100 | >100 | >100 |
| Staphylococcus epidermidis 3519 | 0.39 | 6.2 | 0.39 | 3.1 |
| Enterococcus faecium ATCC 8043 | 0.05 | 1.56 | 0.1 | 0.78 |
| Streptococcus bovis A-5169 | 0.02 | 0.39 | 0.02 | 0.2 |
| Streptococcus agalactiae CMX 508 | 0.05 | 0.39 | 0.05 | 0.78 |
| Streptococcus pyogenes EES61 | 0.05 | 0.39 | <=0.005 | 0.39 |
| Streptococcus pyogenes 930 | >100 | >100 | >100 | >100 |
| Streptococcus pyogenes PIU 2548 | 6.2 | 6.2 | 3.1 | 0.78 |
| Micrococcus luteus ATCC 9341 | 0.05 | 0.2 | 0.1 | 0.39 |
| Micrococcus luteus ATCC 4698 | 0.2 | 1.56 | 0.39 | 0.78 |
| Escherichia coli JUHL | >100 | >100 | 50 | >100 |
| Escherichia coli SS | 0.78 | 1.56 | 0.78 | 0.78 |
| Escherichia coli DC-2 | >100 | >100 | 25 | >100 |
| Candida albicans CCH 442 | >100 | >100 | >100 | >100 |
| Mycobacterium smegmafis ATCC 114 | 3.1 | 1.56 | 3.1 | 25 |
| Nocardia Asteroides ATCC9970 | 0.1 | 0.39 | 0.1 | 0.78 |
| Haemophilis Influenzae DILL AMP R | 4 | 32 | 2 | 16 |
| Streptococcus Pheumoniae ATCC6303 | 0.06 | 1 | 0.06 | 1 |
| Streptococcus Pheumoniae GYR 1171 | 0.06 | 0.5 | 0.03 | 0.25 |
| Streptococcus Pheumoniae 5979 | >128 | >64 | >128 | >128 |
| Streptococcus Pheumoniae 5649 | 16 | 4 | 4 | 0.5 |

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: AIBN for azobisisobutyronitrile; $Bu_3SnH$ for tributyltin hydride; CDI for carbonyldiimidazole; THF for tetrahydrofuran.

Preparation of the Compounds of the Invention

The compounds of the present invention are prepared according to the representative methods described in Schemes 1–4 below, which follow the text describing the Schemes.

Scheme 1 illustrates the preparation of compounds of formulas (I), i.e., compounds (6). These compounds are also useful as starting materials for the preparation of compounds of formulas (II) and (III).

Erythromycin A (1), available from Abbott Laboratories, is first protected at the C-9 carbonyl position to give a compound (2). The preparation of protected erythromycin A is described in the following United States patents. U.S. Pat.

Nos. 4,990,602; 4,331,803, 4,680,368, and 4,670,549 which are incorporated by reference. Also incorporated by reference is European Patent Application EP 260,938. In general, the C-9-carbonyl group of compound (1) is protected as an oxime. (V is =N—O—R$^1$ or =N—O—C(R$^2$)(R$^3$)—O—R$^1$, wherein R$^1$ is selected from the group consisting of (c-1) C$_1$-C$_6$-alkyl, (c-2) Cl-C$_6$-alkyl substituted with one or more groups selected from the group consisting of (c-2-a) aryl, (c-2-b) substituted aryl, (c-d-c) heteroaryl, (c-2-d) substituted heteroaryl, (c-2-e) heterocycloalkyl, and (c-2-f) C$_1$-C$_6$-alkoxy. R$^2$ and R$^3$ are each independently selected from the group consisting of (a) hydrogen, (b) unsubstituted C$_1$-C$_{12}$-alkyl, (c) C$_1$-C$_{12}$-alkyl substituted with aryl, and (d) C$_1$-C$_{12}$-alkyl substituted with substituted aryl, or R$^2$ and R$^3$ taken together with the carbon to which they are attached form a C$_3$-C$_{12}$-cycloalkyl ring. An especially preferred carbonyl protecting group V is O-(1-isopropoxycyclohexyl) oxime.

The 2'-hydroxy and optionally the 4"-hydroxy group of (2) are then protected by reaction with a suitable hydroxy protecting reagent, such as those described by T. W. Greene and P. G. M. Wuts in *Protective Groups in Organic Synthesis*, 2nd ed., John Wiley & Son, Inc., 1991, which is incorporated by reference, for example, acetic anhydride, benzoic anhydride, benzyl chloroformate, hexamethyl disilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of (2) may be accomplished sequentially or simultaneously to provide compound (3) where R$^{p'}$ is a hydroxy protecting group. A preferred protecting group R$^{p'}$ is trimethylsilyl.

The 6-hydroxy group of compound (3) is then fluoromethylated by reaction with bromofluoromethane in the presence of base to give compound (4). Examples of the useful solvents for the reaction are aprotic solvents such as dimethylsulfoxide, diethylsulfoxide, N,N-dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like.

Compound (4) is then converted into an unprotected oxime compound (5) by treatment with an organic acid in a suitable solvent or water/solvent mixture. Examples of suitable solvents are methanol, ethanol, propanol, isopropanol, acetonitrile or an aqueous mixture of one or more of the mentioned solvents.

Intermediate compound (5) rapidly undergoes ring closure under the acidic conditions of the de-oximation step described above to form the 6,9-bridged compound (6), which is a compound of formula (I) of the invention. However, additional acid may be added to ensure the completion of the reaction. Ambient temperature is sufficient for this reaction. Acids which may be used include hydrochloric acid, sulfuric acid, formic acid, acetic acid, chloroacetic acid, and the like.

In Scheme 2 is described the process whereby compound (6) is converted into compounds (II) and (III) of the invention. The 2'-hydroxy and optionally the 4"-hydroxy group of (6) are first protected by reaction with a suitable hydroxy protecting reagent, as described previously, to give compound (7). Compound (7) is then converted to the cyclic compound (8), which is a compound of formula (II) of the invention wherein R$^{p'}$ is a hydroxy protecting group, by reaction with carbonyldiimidazole and sodium hexamethyldisilazine. Cyclic carbonates of formula (II) may also prepared from (7) by reaction with an alkali metal hydride, such as sodium hydride or lithium hydride, and a carbonylating reagent, such as phosgene, diphosgene or triphosgene, under anhydrous conditions followed by aqueous work up. Compound (9), a compound of formula (II) of the invention wherein R$^p$ is H, may be prepared from compound (8) by deprotection of the 2'-hydroxy group according to methods described Greene and Wuts (op. cit.).

Also according to Scheme 2, Compound (7) is converted to the cyclic compound (10) by reaction with formaldehyde in the presence of an acid, or with chloroiodomethane in the presence of base (according to the procedure of Hunt et al., *J. Antibiotics*, (1988), 41: 1644). Compound (10) is a compound of formula (II) of the invention wherein R$^{p'}$ is a hydroxy protecting group. Compound (11), a compound of formula (II) of the invention wherein R$^p$ is H, may be prepared from compound (10) by deprotection of the 2'-hydroxy group according to methods described Greene and Wuts (op. cit.).

In Scheme 3 are described processes for preparation of compounds of formulas (II) wherein Z is other than cladinose. The cladinose moiety may be removed from compounds of formula (II) (compound (8)) either by mild aqueous acid hydrolysis or by enzymatic hydrolysis to give the descladinose compound (19), which is a compound of formula (II) wherein Z is hydroxy. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably –10° to 35° C.

The 3-hydroxy group of a compound of formula (II) wherein Z is hydroxy (19) can then be protected to give a compound of formula (II) wherein Z is a protected hydroxyl group (not shown)) using a suitable hydroxy protecting reagent such as acetic anhydride, benzoic anhydride, benzyl chloroformate or trialkylsilyl chloride in an aprotic solvent, as defined above, preferably dichloromethane, chloroform, DMF, tetrahydrofuran (THF), N-methyl pyrrolidinone or a mixture thereof. A particularly preferred protecting group R$^p$ is benzoate.

Alternately, the 3-hydroxy group of a compound of formula (II) wherein Z is hydroxy (19) may be oxidized to the ketone a compound of formula (II) wherein Y and Z taken together with the atom to which they are attached to form an oxo group (compound 20) using a modified Swern oxidation procedure. Suitable oxidizing agents are N-chlorosuccinimidedimethyl sulfide or carbodiimide-dimethylsulfoxide. In a typical example, (19) is added into a pre-formed N-chlorosuccinimide and dimethyl sulfide complex in a chlorinated solvent such as methylene chloride at –10° to 25° C. After being stirred for about 0.5 to about 4 hours, a tertiary amine such as triethylamine or Hunig's base is added to produce the desired compound (20).

To prepare compounds of formula (II) wherein Y and Z are both H, compound (19) is dissolved in an aprotic solvent such as THF, then reacted with an excess of NaH at from 0° to −30° C. under an inert atmosphere, followed by reaction of the intermediate anion with $CS_2$ and $CH_3I$ at −5° to 10° C., to form a 3-O-xanthyl compound (21). This xanthate intermediate is then reacted with 1.1–1.3 equivalents of $Bu_3SnH$ under an inert atmosphere in the presence of a catalytic amount of AIBN or other suitable radical initiator, in a solvent suitable for a free radical reaction, such as benzene or toluene, for example, at reflux conditions to afford the desired compound (22) of formula (II) wherein Y and Z are both H.

In Scheme 4 are described processes for preparation of compounds of formulas (III) wherein Z is other than cladinose. The processes illustrated are analogous to the processes described in Scheme 3 for preparing compounds of formula (II). Thus, the cladinose moiety may be removed from compounds of formula (III) (compound (10)) either by mild aqueous acid hydrolysis or by enzymatic hydrolysis to give the descladinose compound (23), which is a compound of formula (III) wherein Z is hydroxy.

The 3-hydroxy group of a compound of formula (III) wherein Z is hydroxy (23) can then be protected to give a compound of formula (III) wherein Z is a protected hydroxyl group (not shown)).

Alternatively, the 3-hydroxy group of a compound of formula (III) wherein Z is hydroxy (23) may be oxidized to the ketone a compound of formula (III) wherein Y and Z taken together with the atom to which they are attached to form an oxo group (compound 24).

To prepare compounds of formula (III) wherein Y and Z are both H, compound (23) is converted to the 3O-xanthyl compound (25), and this xanthate intermediate is then reduced with $Bu_3SnH$ to afford the desired compound (26). The methods are as described for Scheme 3.

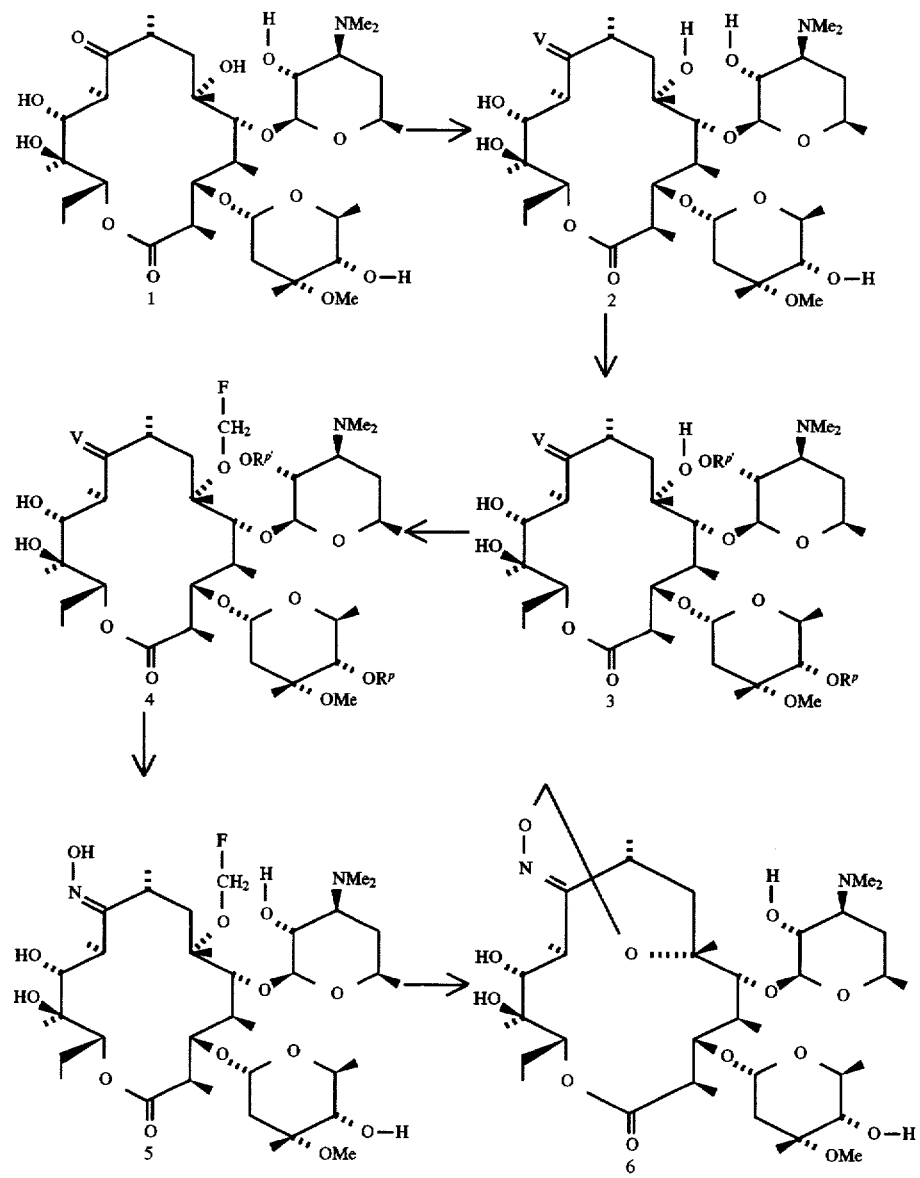

Scheme 1

Scheme 2
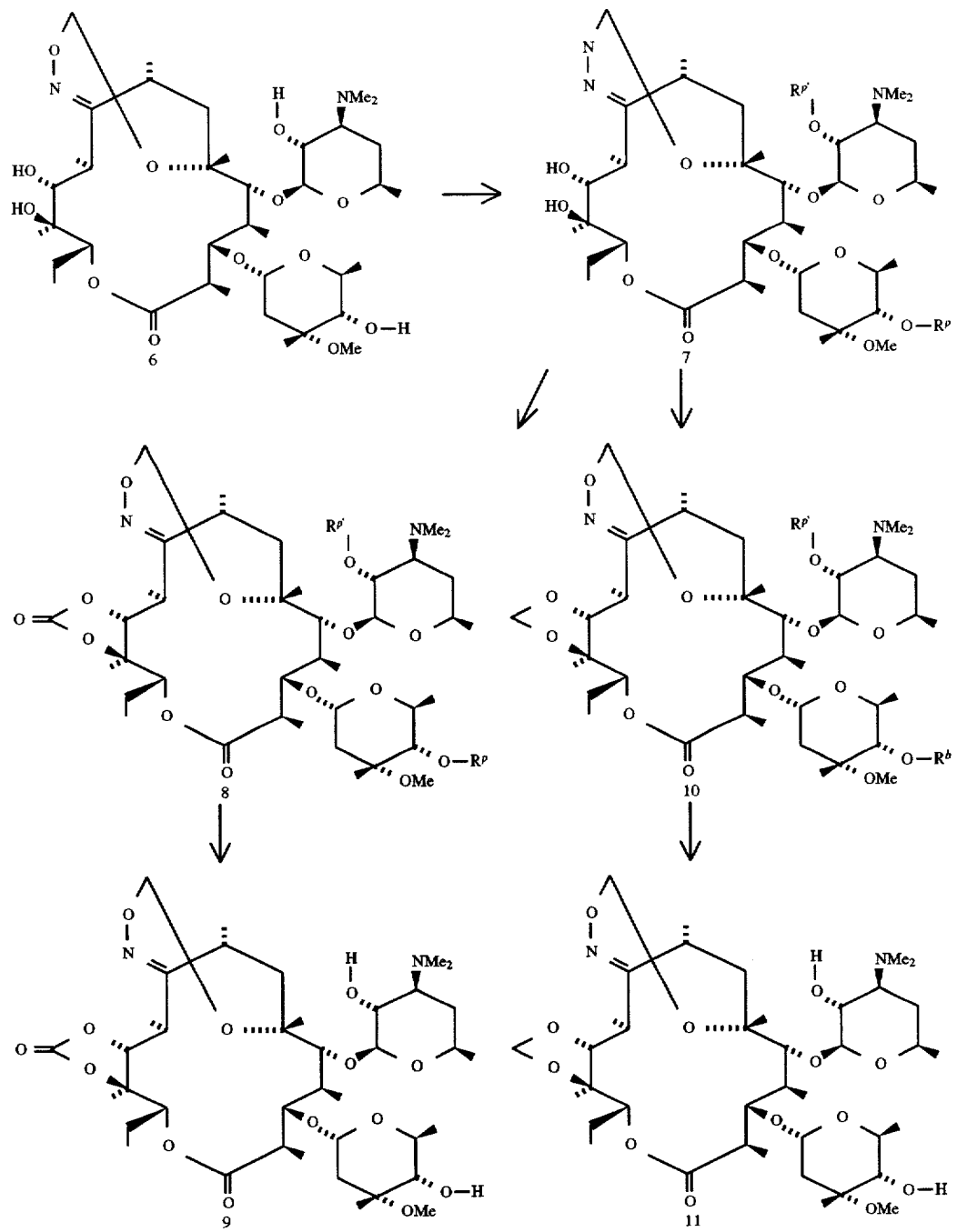

Scheme 3
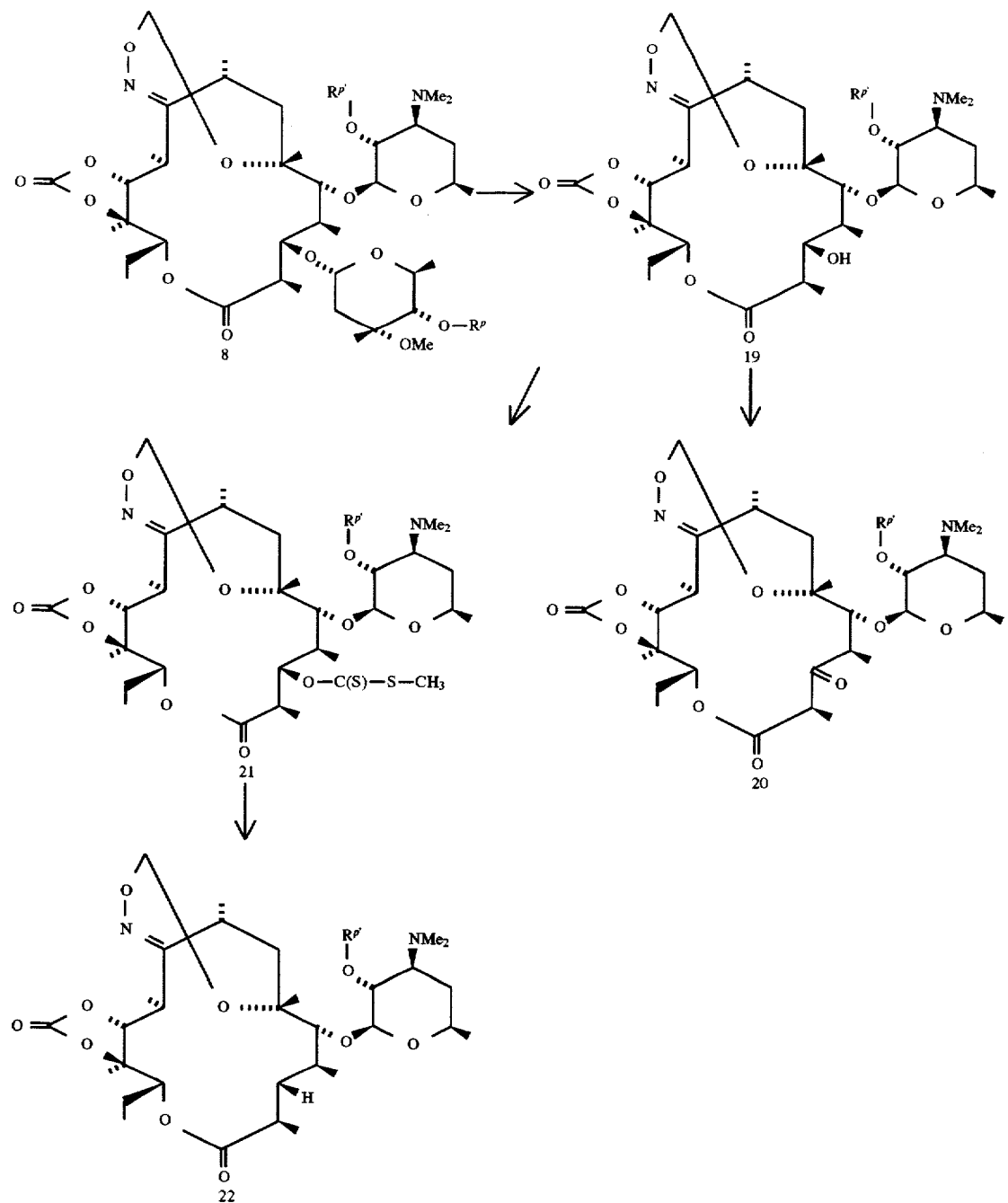

Scheme 4

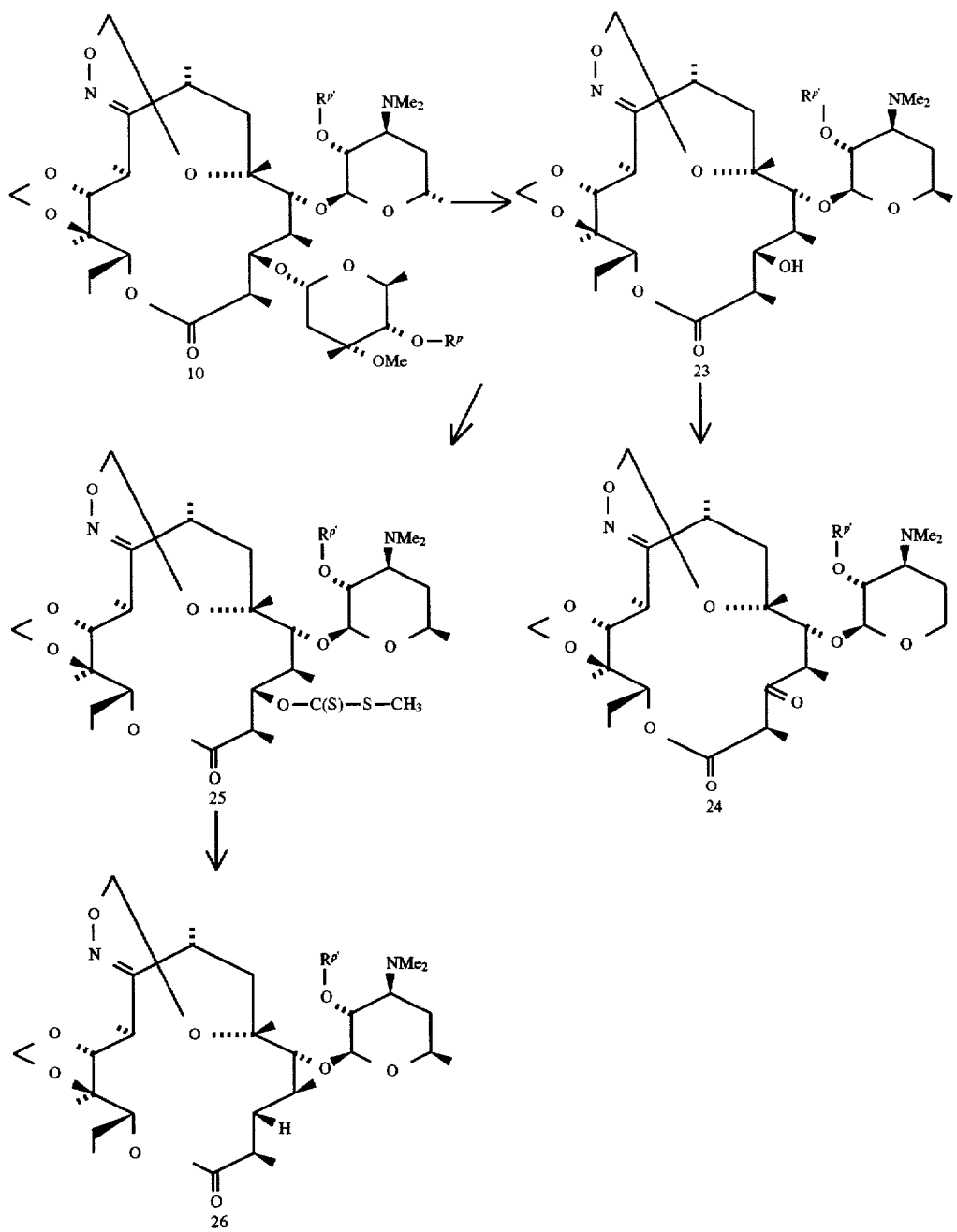

The foregoing Schemes may be better understood by reference to the following examples, which are presented for illustration and not to limit the scope of the inventive concept.

EXAMPLES

The procedures described above for preparing the compounds of the present invention will be better understood in connection with the following examples, which are intended as an illustration of and not a limitation upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

Example 1

Compound of formula (I) Rp is H, Y is H, Z is cladinose

Step 1a: Compound (4) from Scheme 1; V is N—O-(1-isopropoxycyclohexyl), R is fluoromethyl; $R^p$ is trimethylsilyl To a 0° C. solution of 2',4"-bis-O-trimethylsilylerythromycin A 9-|O-(1- isopropoxycyclohexyl)oxime (Compound 3) of Scheme 1, 15 g.14.5 mmol, prepared according to the method of U.S. Pat. No. 4.990.602) in 150 mL of 1:1 THF/DMSO under nitrogen was added bromofluoromethane (2.4 mL, 34.9 mmol). A second solution of potassium tert-butoxide (1M in 1:1 THF/DMSO, 25.4 mL) was added dropwise over 5 hours at 0° C. under nitrogen. The reaction mixture was held in a freezer overnight, then quenched with allylamine at 0° C. for 5 minutes. The mixture was diluted with water and extracted with ethyl acetate. The organic phase was washed with water and brine, dried over $MgSO_4$, and concentrated in vacuo to give the desired compound (16.25 g). MS APCI m/e 731 $(M+H)^+$.

Step 1b: Compound of formula (I) $R^p$ is H, Y is H, Z is cladinose

To a solution of the compound from Step 1a (16 g) in acetonitrile (60 mL) and water (30 mL) was added acetic acid (45 mL) at ambient temperature. After 30 hours at ambient temperature, the reaction mixture was held at 0° C. for 16 hours and concentrated under vacuum at 40° C. The residue was chased twice with toluene and dried to constant weight (13.7 g). The residue was purified by chromatography on silica gel, eluting with 1:98:1 methanol/dichlomethane/ammonium hydroxide to give the title compound (510 mg) which was crystallized from acetonitrile. $^{13}C$ NMR ($CDCl_3$) δ 175.3(C-1), 44.7(C-2), 16.4(C-2Me), 79.9(C-3), 38.9(C-4), 9.2(C-4Me), 82.0(C-5), 80.7(C-6), 19.7(C-6Me), 38.2(c-7), 28.6(C-8), 16.7(C-8Me), 188.3(C-9), 33.6(C-10), 12.7(C-10Me), 72.5(C-11), 74.7(C12), 16.3 (C-12Me), 77.6(C-13), 20.7(C-14), 10.6(C-15), 102.3(C-1'), 70.9(C-2'), 65.5(C-3'), 40.1(C-3'NMe), 28.5(C-4'), 68.6(C-5'), 21.4(C-6'), 96.2(C-1"), 35.1(C-2"), 72.7(C-3"), 49.4(C-3"OMe), 21.4(C-3"Me), 77.9(C-4"), 65.4(C-5"), 18.6(C-6"), 89.5(dioxy methylene). MS FAB High Resolution $(M+H)^+$: calcd for $C_{38}H_{69}N_2O_{13}$: 761.4800; observed: 761.4797.

Example 2

Compound of formula (II) $R^p$ is H, Y is H, Z is cladinose

Step 2a: Compound (7) of Scheme 2, $R^p$ is trimethylsilyl

To a solution of the compound from Step 1b (280 mg) in dry dichloromethane (7 mL) under nitrogen at ambient temperature was added a solution of trimethylsilyl chloride (0.070 mL) and trimethylsilylimidazole (0.081 mL) in dry dichloromethane (1.3 mL). After 30 minutes, the reaction was quenched with saturated aqueous sodium bicarbonate solution, and the mixture was extracted with ethyl acetate. The organic phase was washed with water and brine, dried over $MgSO_4$, and concentrated in vacuo to give the desired compound (318 mg). MS ESI m/e: 905 $(M+H)^+$.

Step 2b: Compound (8) of Scheme 2, $R^p$ is trimethylsilyl

To a −40° C. solution of the compound from Step 2a (300 mg) in dry THF (7.5 mL) was added 1M sodium trimethylsilylamide (0.386 mL). The mixture was stirred for 10 minutes, and a separate solution of carbonyldiimidazole (212 mg) in THF (3.5 mL) was added. The mixture was then stirred for 5 minutes at room temperature and for 15 minutes at 22° C. The mixture was cooled to 0° C., quenched with 1M sodium dihydrogen phosphate solution, and extracted with ethyl acetate. The organic phase was washed with water and brine, dried over $MgSO_4$, and concentrated in vacuo to give the desired compound (335 mg). MS ESI m/e: 931 $(M+H)^+$.

Step 2c: Compound of formula (II) $R^p$ is H, Y is H, Z is cladinose

A sample of the compound from Step 2b (330 mg) was stirred in a solution of water (0.5 mL) and acetic acid (0.25 mL) in acetonitrile (2 mL) for 2 hours. The mixture was diluted with ethyl acetate and washed with saturated aqueous sodium bicarbonate solution. The organic phase was washed with water and brine, dried over $MgSO_4$, and concentrated in vacuo. The residue was re-treated with the same procedure (4 hours) to hydrolyse remaining protecting groups. The product was re-isolated as described, then purified by chromatography on silica gel, eluting with 1:98:1 methanol/dichlomethane/ammonium hydroxide to give the title compound (78 mg). $^{13}C$ NMR ($CDCl_3$) δ 82.6(C-9), 175.4(C-1), 153.4(carbonate carbonyl carbon), 102.9, 96.2, 88.6, 85.8, 84.0, 82.8, 80.3, 79.7, 77.9, 76.8, 72.6, 70.9, 68.9, 65.6, 65.4, 49.4, 44.9, 40.2, 39.6, 39.2, 34.9, 34.4, 28.6, 28.5, 21.8, 21.5,21.4, 19.8, 18.6, 17.8, 16.5, 15.9, 15.5, 9.9, 9.2. MS FAB High Resolution $(M+H)^+$: calcd: 787.4592; observed: 787.4606.

Example 3

Compound of formula (II), $R^p$ is H, Y and Z taken together with the atom to which they are attached form an oxo group Step 3a: Compound (19) of Scheme 3, $R^p$ is H To a 0° C. solution of the compound from Example 2 (compound (9) of Scheme 2, 1.36 g) in 1:2 ethanol/water (27.8 mL) was added 1M HCl (3.1 mL) over several minutes. The mixture was stirred at room temperature for 9 hours, refrigerated overnight, then stirred at room temperature for another 6 hours. The mixture was diluted with ethyl acetate. The organic phase was separated, washed with saturated aqueous sodium bicarbonate solution and brine, dried over $MgSO_4$ and concentrated. The residue was purified by chromatography on silica gel, eluting with 1:98:1 methanol/dichlomethane/ammonium hydroxide to give the title compound (620 mg). $^{13}C$ NMR ($CDCl_3$) δ 183.1(C-9), 175.0(C-1), 153.6(carbonate carbonyl carbon), 106.1, 92.0, 89.3, 88.9, 85.2, 84.0, 80.2, 78.2, 76.0, 70.6, 70.2, 65.5, 44.3, 40.2, 37.9, 37.7, 34.0, 28.4, 28.1, 21.8, 21.2, 18.6, 17.2, 15.2, 14.4, 14.0, 9.9, 8.2. MS ESI m/e: 629 $(M+H)^+$.

Step 3b: Compound (19) of Scheme 3, $R^p$ is benzoyl

To a solution of the compound from Step 3a (615 mg) in dichloromethane (5 mL) was added benzoic anhydride (354 mg). After 10 minutes, triethylamine (0.218 mL) was added, and the mixture was stirred for 40 hours under nitrogen at ambient temperature. The reaction was quenched with aqueous sodium bicarbonate solution, and the mixture was extracted with ethyl acetate. The organic phase was washed with water and brine, dried over $MgSO_4$, and concentrated. The residue was purified by chromatography on silica gel, eluting with 25% acetone/hexanes to give the title compound (550 mg). MS ESI m/e: 733 $(M+H)^+$.

Step 3c: Compound (20) of Scheme 3, $R^p$ is benzoyl

To a −10° C. solution of N-chlorosuccinimide (168 mg) in dichloromethane (4.5 mL) under nitrogen was added dimethyl sulfide (0.108 mL) over 10 minutes. To this solution was added a solution of the compound from Step 3b (530 mg) in dichloromethane (6 mL) over 25 minutes, and the mixture was stirred at −10° to −5° C. for 30 minutes. Triethylamine (0.117 mL) was added, and the mixture was stirred under nitrogen at −10° to −5° C. for 40 minutes. The reaction was quenched with aqueous sodium bicarbonate solution, and the mixture was extracted with ethyl acetate. The organic phase was washed with water and brine, dried over $MgSO_4$, and concentrated to give the title compound (490 mg). $^{13}C$ NMR ($CDCl_3$) δ 204.98(C-3), 180.82(C-9), 168.61(C-1), 165.26, 152.79 (carbonate carbonyl carbon), 132.86, 130.45, 129.66, 128.33, 101.87, 88.05, 87.16, 84.0, 81.92, 79.10, 78.10, 76.58, 71.97, 69.35, 63.80, 50.90, 46.06, 40.74, 40.58, 35.24, 31.12, 28.66, 22.16, 20.96, 20.54, 19.60, 18.91, 17.76, 14.36, 12.73, 9.49. MS APCI m/e: 731 (M+H)$^+$.

Step 3d: Compound of formula (II), R$^p$ is H, Y and Z taken together with the atom to which they are attached form an oxo group A solution of the compound of Step 3c (490 mg) in methanol (12 mL) was stirred under nitrogen at reflux temperature for 3 hours and at room temperature overnight. The solvent was removed, and the residue was purified by chromatography on silica gel, eluting with 1:1 acetone/hexanes to give the title compound (375 mg). $^{13}$C NMR (CDCl$_3$) δ 204.7(C-3), 180.81(C-9), 168.63(C-1), 152.80 (carbonate carbonyl carbon), 104.04, 88.01, 87.15, 84.22, 82.67, 79.01, 76.58, 70.36, 69.70, 65.93, 50.98, 46.76, 41.14, 40.19, 35.41, 28.76, 28.19, 22.22, 21.10, 20.61, 19.67, 19.04, 17.88, 14.36, 13.12, 9.51. MS FAB High Resolution (M+H)$^+$: calculated: 627.3493; observed: 627.3478.

Example 4

Compound of formula (III), R$^p$ is H, Y is H and Z is hydroxy

A sample of the compound from Example 2, Step 2a is treated with chloroiodomethane in the presence of base according to the procedure of Hunt et al., *J. Antibiotics*, (1988), 41: 1644, hydrolyzed with HCl in ethanol, then the hydrolyzed compound is heated with methanol to give the title compound.

Example 5

Compound of formula (III), R$^p$ is H, Y and Z are H

Step 5a. Compound of formula (III), R$^p$ is H, Y is H and Z is O-xanthyl

A sample of the compound from Example 4 is treated with an excess of NaH at from 0° to −30° C. under an inert atmosphere, followed by reaction of the intermediate anion with CS$_2$ and CH$_3$I at −5° to 10° C., to form the xanthate intermediate. The xanthate intermediate is reacted with 1.1–1.3 equivalents of Bu$_3$SnH under an inert atmosphere in the presence of a catalytic amount of AIBN in refluxing toluene to afford a compound in which Rp is trimethylsilyl. This compound is then heated with methanol to give the title compound.

Example 6

Compound of formula (III), R$^p$ is H, Y and Z taken together with the atom to which they are attached form an oxo group A sample of the compound of Example 4 is treated according to the procedures of Example 3 to give the title compound.

What is claimed is:

1. A compound selected from the group consisting of:

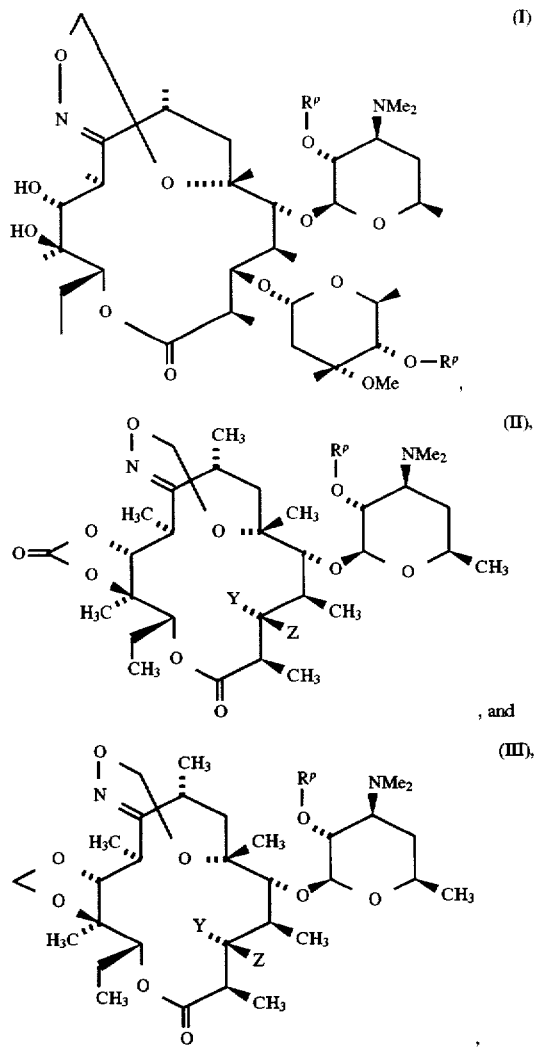

as well as the pharmaceutically acceptable salts, esters and prodrugs thereof, wherein R$^p$ is hydrogen or a hydroxy protecting group;
one of Y and Z is H and the other is selected from the group consisting of hydrogen, hydroxy, protected hydroxy and —O-cladinose, or Y and Z are taken together with the atom to which they are attached to form an oxo group.

2. A compound according to claim 1 which is selected from the group consisting of:
Compound of formula (I) Rp is H;
Compound of formula (II) R$^p$ is H, Y is H, Z is cladinose;
Compound of formula (II), R$^p$ is H, Y and Z taken together with the atom to which they are attached form an oxo group,
Compound of formula (III), R$^p$ is H, Y is H and Z is hydroxy; and
Compound of formula (III), R$^p$ is H, Y and Z are H; and
Compound of formula (III), R$^p$ is H, Y and Z taken together with the atom to which they are attached form an oxo group.

3. A pharmaceutical composition for treating bacterial infections comprising a therapeutically effective amount of a compound of claim 1 or a pharmaceutically acceptable salt or ester thereof in combination with a pharmaceutically acceptable carrier.

4. A method for treating bacterial infections comprising administering to a mammal in need of such treatment a pharmaceutical composition containing a therapeutically-effective amount of a compound of claim 1 or a pharmaceutically acceptable salt or ester thereof.

5. A compound according to claim 1 having the formula (I)

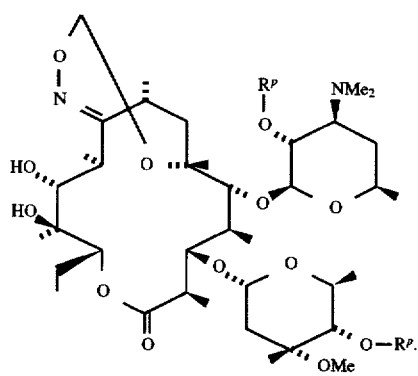

(I)

6. A process for preparing a compound having the formula (I)

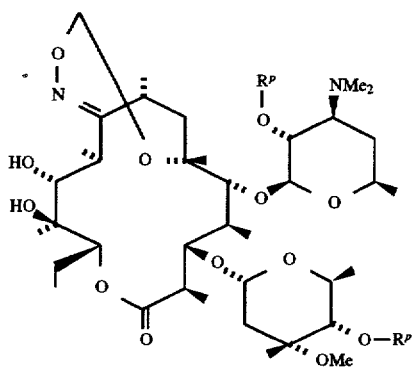

(I)

wherein $R^p$ is hydrogen or a hydroxy protecting group; the method comprising:

(a) reacting a compound having the formula

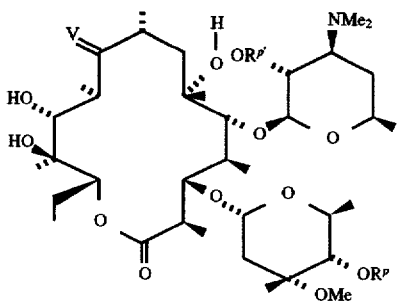

wherein $R^{p'}$ is a hydroxy protecting group; and
V is =N—O—$R^1$ or =N—O—C($R^2$)($R^3$)—O—$R^1$, wherein
$R^1$ is selected from the group consisting of:
(C-1) $C_1$–$C_6$-alkyl.
(c-2) $C_1$–$C_6$-alkyl substituted with one or more groups selected from the group consisting of
(c-2-a) aryl,
(c-2-b) substituted aryl,
(c-d-c) heteroaryl,
(c-2-d) substituted heteroaryl,
(c-2-e) heterocycloalkyl,
(c-2-f) $C_1$–$C_6$-alkoxy, $R^2$ and $R^3$ are each independently selected from the group consisting of
(a) hydrogen,
(b) unsubstituted $C_1$–$C_{12}$-alkyl,
(c) $C_1$–$C_{12}$-alkyl substituted with aryl, and
(d) $C_1$–$C_{12}$-alkyl substituted with substituted aryl, or $R^2$ and $R^3$ taken together with the carbon to which they are attached form a $C_3$–$C_{12}$-cycloalkyl ring;

with bromofluoromethane in the presence of base to give a compound having the formula

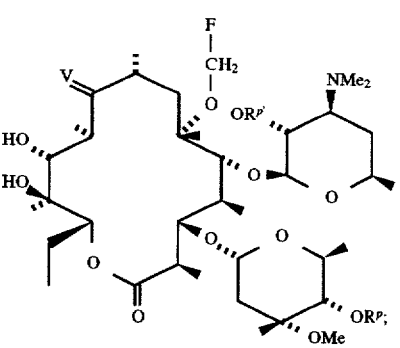

(b) treating the compound from Step (a) hydrolytically with acid to give a compound having the formula

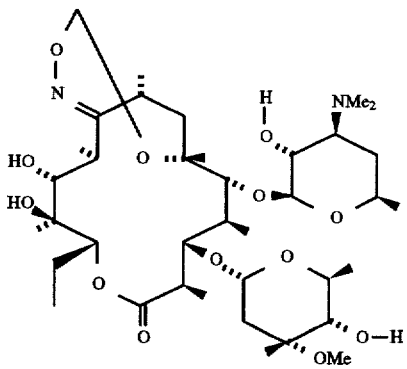

(c) optionally treating the compound from Step (b) with a hydroxy protecting reagent to give the desired compound wherein $R^p$ is a hydroxy protecting group.

7. A compound according to claim 1 having the formula (II)

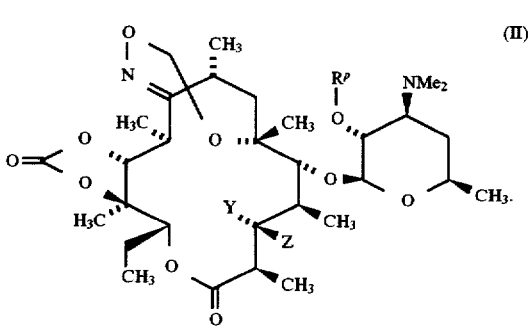

(II)

8. A process for preparing a compound having the formula (II)

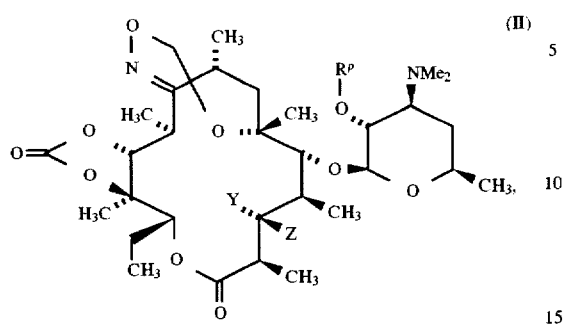

(II)

wherein

R$^p$ is hydrogen or a hydroxy protecting group;

one of Y and Z is H and the other is selected from the group consisting of hydrogen, hydroxy, protected hydroxy and —O-cladinose, or Y and Z are taken together with the atom to which they are attached to form an oxo group, the method comprising:

(a) reacting a compound having the formula

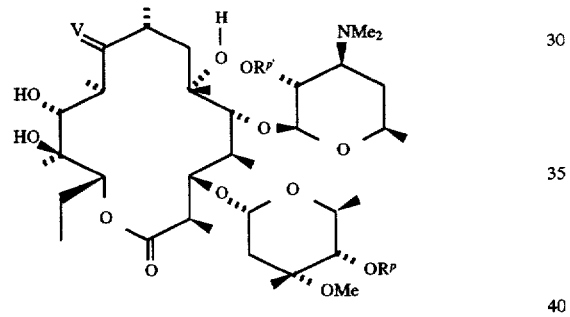

wherein R$^{p'}$ is a hydroxy protecting group; and

V is =N—O—R$^1$ or =N—O—C(R$^2$)(R$^3$)—O—R$^1$, wherein

R$^1$ is selected from the group consisting of:
(c-1) C$_1$–C$_6$-alkyl,
(c-2) C$_1$–C$_6$-alkyl substituted with one or more groups selected from the group consisting of
(c-2-a) aryl,
(c-2-b) substituted aryl,
(c-d-c) heteroaryl,
(c-2-d) substituted heteroaryl,
(c-2-e) heterocycloalkyl,
(c-2-f) C$_1$–C$_6$-alkoxy, R$^2$ and R$^3$ are each independently selected from the group consisting of
(a) hydrogen,
(b) unsubstituted C$_1$–C$_{12}$-alkyl,
(c) C$_1$–C$_{12}$-alkyl substituted with aryl, and
(d) C$_1$–C$_{12}$-alkyl substituted with substituted aryl, or R$^2$ and R$^3$ taken together with the carbon to which they are attached form a C$_3$–C$_{12}$-cycloalkyl ring;

with bromofluoromethane in the presence of base to give a compound having the formula

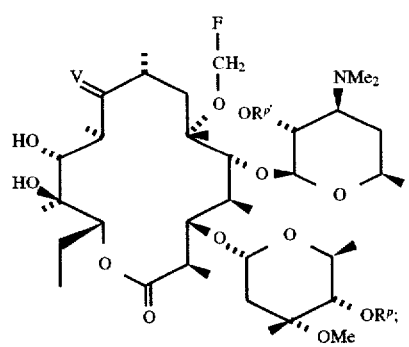

(b) treating the compound from Step (a) hydrolytically with acid to give a compound having the formula

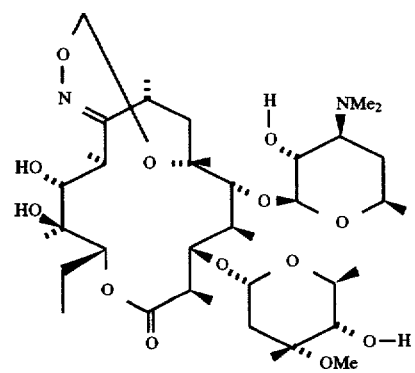

(c) treating the compound from Step (b) with a hydroxy protecting reagent to give the desired compound wherein R$^{p'}$ is a hydroxy protecting group (d) treating a compound from Step (c) with a reagent selected from the group consisting of
(i) carbonyldiimidazole and sodium hexamethyldisilazine, and
(ii) an alkali metal hydride and a carbonylating reagent under anhydrous conditions, to give a compound of formula (II) wherein Y is H, Z is cladinose and R$^{p'}$ is a hydroxy protecting group;

(e) optionally hydrolytically treating with acid a compound of formula (II) wherein Y is H, Z is cladinose and R$^{p'}$ is a hydroxy protecting group (the compound from Step (d)) to give a compound of formula (II) wherein Y is H, Z is hydroxy and R$^p$ is a hydroxy protecting group;

(f) optionally treating a compound of formula (II) wherein Y is H, Z is hydroxy and R$^{p'}$ is a hydroxy protecting group (the compound from Step (e)) with a hydroxy protecting reagent to give a compound of formula (II) Y is H, Z is protected hydroxy, and R$^{p'}$ is a hydroxy protecting group;

(g) optionally oxidizing a compound of formula (II) wherein Y is H, Z is hydroxy and R$^{p'}$ is a hydroxy protecting group (the compound from Step (e)) to give a compound of formula (II) wherein Y and Z are taken together with the atom to which they are attached to form an oxo group and R$^{p'}$ is a hydroxy protecting group;

(h) optionally treating a compound of formula (II) wherein Y is H, Z is hydroxy and R$^{p'}$ is a hydroxy protecting group (the compound from Step (e)) with an excess of NaH in an aprotic solvent followed by reaction of the intermediate anion with $CS_2$ and $CH_3I$ to form a xanthate intermediate which is then treated with $Bu_3SnH$ under an inert atmosphere in the presence of a catalytic amount of a suitable radical initiator to afford the desired compound of formula (II) wherein Y and Z are H and $R^{p'}$ is a hydroxy protecting group;

(i) optionally deprotecting to give a compound of formula (II) wherein $R^{p'}$ is H; and isolating the desired compound.

9. A compound according to claim 1 having the formula (III)

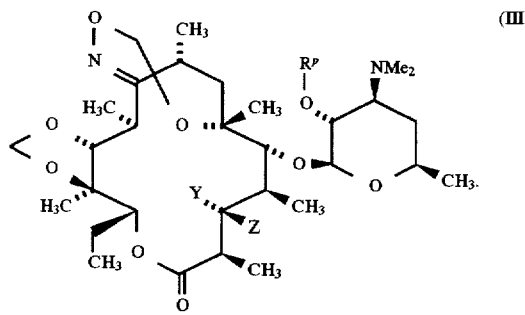

A process for preparing a compound having the formula (III)

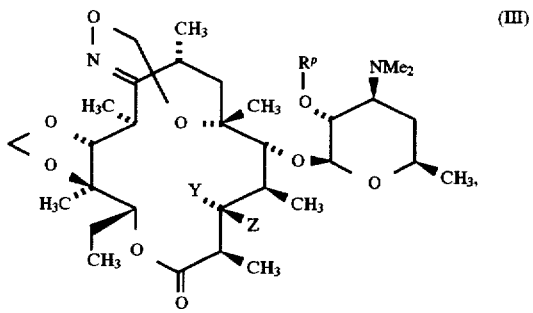

wherein $R^p$ is hydrogen or a hydroxy protecting group;
one of Y and Z is H and the other is selected from the group consisting of hydrogen, hydroxy, protected hydroxy and —O-cladinose, or Y and Z are taken together with the atom to which they are attached to form an oxo group, the method comprising:

(a) reacting a compound having the formula

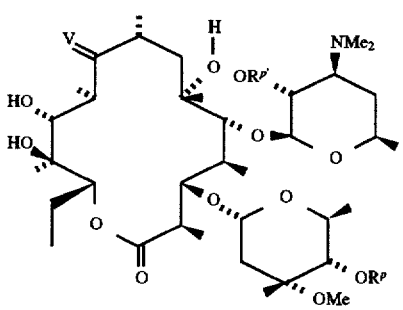

wherein $R^{p'}$ is a hydroxy protecting group; and

V is $=N-O-R^1$ or $=N-O-C(R^2)(R^3)-R^1$, wherein $R^1$ is selected from the group consisting of:

(c-1) $C_1-C_6$-alkyl, (c-2) $C_1-C_6$-alkyl substituted with one or more groups selected from the group consisting of (c-2-a) aryl,
(c-2-b) substituted aryl,
(c-d-c) heteroaryl,
(c-2-d) substituted heteroaryl,
(c-2-e) heterocycloalkyl,
(c-2-f) $C_1-C_6$-alkoxy, $R^2$ and $R^3$ are each independently selected from the group consisting of (a) hydrogen,
(b) unsubstituted $C_1-C_{12}$-alkyl,
(c) $C_1-C_{12}$-alkyl substituted with aryl, and
(d) $C_1-C_{12}$-alkyl substituted with substituted aryl, or $R^2$ and $R^3$ taken together with the carbon to which they are attached form a $C_3-C_{12}$-cycloalkyl ring;

with bromofluoromethane in the presence of base to give a compound having the formula

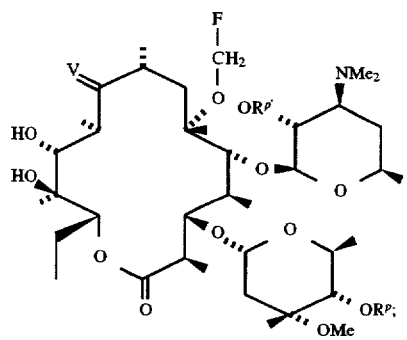

(b) treating the compound from Step (a) hydrolytically with acid to give a compound having the formula

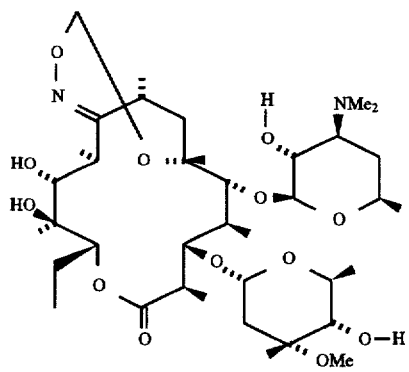

(c) treating the compound from Step (b) with a hydroxy protecting reagent to give the desired compound wherein $R^{p'}$ is a hydroxy protecting group;

(d) treating a compound from Step (c) with a reagent selected from the group consisting of (i) formaldehyde in the presence of an acid, and
(ii) chloroiodomethane in the presence of base to give a compound of formula (III) wherein Y is H, Z is cladinose and $R^{p'}$ is a hydroxy protecting group;

(b) optionally hydrolytically treating with acid a compound of formula (III) wherein Y is H, Z is cladinose and $R^{p'}$ is a hydroxy protecting group (the compound from Step (d)) to give a compound of formula (III) wherein Y is H, Z is hydroxy and $R^{p'}$ is a hydroxy protecting group;

(c) optionally treating a compound of formula (11) wherein Y is H, Z is hydroxy and $R^{p'}$ is a hydroxy protecting group (the compound from Step (e)) with a hydroxy protecting reagent to give a compound of formula (III) Y is H, Z is protected hydroxy, and $R^{p'}$ is a hydroxy protecting group;

(d) optionally oxidizing a compound of formula (III) wherein Y is H, Z is hydroxy and $R^{p'}$ is a hydroxy protecting group (the compound from Step (e)) to give a compound of formula (II) wherein Y and Z are taken together with the atom to which they are attached to form an oxo group and $R^{p'}$ is a hydroxy protecting group;

(e) optionally treating a compound of formula (III) wherein Y is H, Z is hydroxy and $R^{p'}$ is a hydroxy protecting group (the compound from Step (e)) with an excess of NaH in an aprotic solvent followed by reaction of the intermediate anion with $CS_2$ and $CH_3I$ to form a xanthate intermediate which is then treated with $Bu_3SnH$ under an inert atmosphere in the presence of a catalytic amount of a suitable radical initiator to afford the desired compound of formula (II) wherein Y and Z are H and $R^{p'}$ is a hydroxy protecting group;

(f) optionally deprotecting to give a compound of formula (III) wherein $R^{p'}$ is H; and isolating the desired compound.

* * * * *

UNITED STATES PATENT AND TRADEMARK OFFICE
CERTIFICATE OF CORRECTION

PATENT NO. : 5,780,605
DATED : July 14, 1998
INVENTOR(S) : Or et al.

It is certified that error appears in the above-identified patent and that said Letters Patent is hereby corrected as shown below:

Column 35, line 65, change " $(R^3)-R^1$ " to -- $(R^3)-O-R^1$ --.

Signed and Sealed this

Second Day of February, 1999

Attest:

Attesting Officer

*Acting Commissioner of Patents and Trademarks*